(12) United States Patent
Lebon et al.

(10) Patent No.: US 12,240,669 B2
(45) Date of Patent: Mar. 4, 2025

(54) RECEPTACLE FOR HOLDING AN ACTIVE SUBSTANCE AND CORRESPONDING CLOSURE AND CONTAINER WITH SUCH A RECEPTACLE

(71) Applicant: AIRNOV, INC., Wilmington, DE (US)

(72) Inventors: Jacquy Lebon, Challands (FR); Valere Logel, Levallois Perret (FR); Dominique Bois, Montreuil aux Lions (FR)

(73) Assignee: AIRNOV, INC., Wilmington, DE (US)

( * ) Notice: Subject to any disclaimer, the term of this patent is extended or adjusted under 35 U.S.C. 154(b) by 517 days.

(21) Appl. No.: 17/595,292

(22) PCT Filed: May 14, 2020

(86) PCT No.: PCT/EP2020/063467
§ 371 (c)(1),
(2) Date: Nov. 12, 2021

(87) PCT Pub. No.: WO2020/229601
PCT Pub. Date: Nov. 19, 2020

(65) Prior Publication Data
US 2022/0315299 A1 Oct. 6, 2022

(30) Foreign Application Priority Data
May 14, 2019 (EP) .................... 19305616

(51) Int. Cl.
*B65D 81/26* (2006.01)
*B01D 53/04* (2006.01)
(Continued)

(52) U.S. Cl.
CPC ......... *B65D 51/30* (2013.01); *B01D 53/0415* (2013.01); *B65D 41/16* (2013.01); *B65D 51/1622* (2013.01); *B65D 81/268* (2013.01)

(58) Field of Classification Search
CPC ...... B65D 51/30; B65D 81/26; B65D 81/264; B65D 81/265; B65D 81/266; B65D 81/268; B65D 81/267; A61J 1/03; A61J 1/1425
(Continued)

(56) References Cited

U.S. PATENT DOCUMENTS 1,621,487 A 3/1927 Aulbach
4,093,105 A 6/1978 Russell et al.
(Continued)

FOREIGN PATENT DOCUMENTS

CN 203997493 U 12/2014
WO 98/51758 A1 11/1998
(Continued)

OTHER PUBLICATIONS

International Search Report with Written Opinion of the International Searching Authority, dated Aug. 5, 2020, with respect to International Application No. PCT/EP2020/063467.
(Continued)

*Primary Examiner* — King M Chu
(74) *Attorney, Agent, or Firm* — Scott R. Cox (57) ABSTRACT

A receptacle forming a chamber partially filled with an active substance, wherein the receptacle is a body and a cap which closes the body. The cap includes a top wall with a first main side facing an interior of the chamber and a skirt formed with the first main side of the top wall. The body includes a bottom wall and a sidewall. The skirt and the sidewall surround one another in contact with each other. The walls surrounding the chamber include the bottom wall, the top wall and either the skirt or the sidewall. At least one ventilation path is provided between the skirt and the sidewall, such that the ventilation path connects the chamber with the outside atmosphere.

19 Claims, 11 Drawing Sheets

(51) Int. Cl.
  *B65D 41/16* (2006.01)
  *B65D 51/16* (2006.01)
  *B65D 51/30* (2006.01)

(58) Field of Classification Search
  USPC .......................................................... 206/204
  See application file for complete search history.

(56) References Cited

U.S. PATENT DOCUMENTS

| | | | |
|---|---|---|---|
| 5,191,721 | A | 3/1993 | Incorvia et al. |
| 5,310,074 | A | 5/1994 | Jochem et al. |
| 5,315,987 | A | 5/1994 | Swann |
| 5,736,616 | A | 4/1998 | Ching et al. |
| 5,759,241 | A * | 6/1998 | Klett ................. B01D 53/261 220/373 |
| 5,894,949 | A * | 4/1999 | Taskis ................. B65D 51/002 215/261 |
| 8,302,792 | B2 | 11/2012 | Logel et al. |
| 8,360,257 | B2 | 1/2013 | Sebille et al. |
| 9,586,738 | B2 | 3/2017 | Herrbach et al. |
| 9,650,184 | B2 | 5/2017 | Fily et al. |
| 10,279,966 | B1 | 5/2019 | Solomon |
| 2006/0011633 | A1* | 1/2006 | Cook ................. B65D 51/1661 215/331 |
| 2008/0264895 | A1 | 10/2008 | Prieto et al. |
| 2016/0046413 | A1* | 2/2016 | Hamdoun .......... B65D 51/1605 215/316 |
| 2018/0118423 | A1 | 5/2018 | Bois et al. |
| 2019/0344938 | A1 | 11/2019 | Lebon |
| 2020/0385182 | A1 | 12/2020 | Lebon et al. |
| 2022/0289457 | A1* | 9/2022 | Romeo ................ B65D 41/485 |

FOREIGN PATENT DOCUMENTS

| | | |
|---|---|---|
| WO | 99/48963 A2 | 9/1999 |
| WO | 2015/139954 A1 | 9/2015 |
| WO | 2018/149778 A1 | 8/2018 |

OTHER PUBLICATIONS

International Preliminary Report on Patentability of the International Searching Authority, dated Nov. 16, 2021, with respect to International Application No. PCT/EP2020/063467.

U.S. Appl. No. 17/595,288, unpublished.

English Translation of Official Action from Chinese Patent Office dated Oct. 31, 2022, in corresponding parallel Chinese Application No. 202080037108.1—cited only for references disclosed therein.

* cited by examiner

Fig. 3
(detail « B »)

Fig. 4

Fig. 5 *(detail « C »)*

RECEPTACLE FOR HOLDING AN ACTIVE SUBSTANCE AND CORRESPONDING CLOSURE AND CONTAINER WITH SUCH A RECEPTACLE

FIELD OF THE INVENTION

The invention relates to a receptacle intended to regulate the atmosphere in a container for storing sensitive products, the receptacle being designed to be at least partially filled with an active substance and permit gases and vapors to enter the receptacle for interacting with the active substance. The invention also relates to a closure for closing an open end of a container body part comprising such receptacle and a container for storing loose products comprising such receptacle.

BACKGROUND OF THE INVENTION

A number of small desiccant receptacles, also called canisters, have been disclosed, which are formed from gas and liquid impermeable body portions which can be perforated and onto which are secured one or more perforated end caps. These canisters generally contain a desiccant material which adsorbs moisture from the air as the air flows through the perforations provided in an end cap of the desiccant canister.

Such canisters are used in containers which are filled with sensitive products like pharmaceuticals, the deterioration of which when exposed to moisture should be prevented.

A common structure of such canisters is a one piece plastic body containing a cylindrical outer wall and a circular bottom wall, onto which is secured a cap.

Mechanically assembled canisters are sometimes problematic in that the mechanical connection between the canister body and the cap might not be strong enough to withstand a deformation of the canister under load conditions. Such load conditions might occur during use in a container filled with particulate matter or under exceptional circumstances, e.g. when the container is inadvertently dropped onto a hard surface. Load conditions leading to a deformation of the canister might also occur during the distribution of the canister in an automatic conditioning device. The resulting undesired opening of the canister upon deformation has the consequence that its contents, e.g. dehydrating agents or oxygen adsorbents, might be introduced into the interior of the container and might contaminate goods contained therein, like drugs.

A different way to manufacture canisters is the assembly of a canister body with a porous membrane by means of the application of heat. When using a heat treatment, welding techniques have been previously suggested. For example a canister with an elongated hollow plastic body can be provided with two caps, which are fused to the ends of the plastic body. Specifically, a manufacturing method was suggested including the steps of applying pressure and vibratory welding energy to the cap to form a fusion bond.

However, the welding or any other comparable heat treatment to a porous membrane might be problematic because either the welded connection is weak or the membrane might be more sensitive to heat than the canister body. Accordingly, a heat treatment of a porous membrane might negatively influence its density, i.e. its permeability, and its behavior at the welded seams due to the degradation of the material of the membrane under an excessive thermal load.

As a further problem, the functional material inside the canister might also be negatively affected by elevated temperatures so that a heat treatment is not feasible under certain circumstances. For example, gas uptake kinetic of chemical adsorbent may be catalyzed by heat.

A mechanical assembly followed by a welding of the contact region between the canister body and the cap involves a further manufacturing step and increases the production costs.

A further technical problem of perforated membranes is that powder active materials can contain particles or pieces of particles which can be friable and/or small enough to pass through the perforations, leading to a contamination of the content of the container in which the canister is introduced.

In other solutions in the prior art, after filling in the active substance, the chamber is closed by a permeable disc, for example made of cardboard, which is fixed to the sidewalls of the chamber by crimping the extremity of the sidewalls of the chamber. One of the major drawbacks of such a solution in the prior art is the additional manufacturing step of attaching the disc and the associated quality control required because a safe attachment of the disc is essential in order to avoid a leakage of the active material and the undesired pollution of the articles contained in the container. In case of drugs, such pollution can be very problematic.

Another technology is to clip the permeable disc instead of crimping it. One of the main drawbacks of such solutions is the possibly insufficient holding force of the permeable disc, resulting in leakage of the absorbent material and pollution of the drugs contained in the container.

DISCLOSURE OF THE INVENTION

It is an object of the invention to provide a receptacle for an active substance which is easy to manufacture, and safely avoids potential leakage of the active substance and allows a sufficient transport of the gaseous substances to be trapped between the outside and the inside of the receptacle.

This object is solved by a receptacle with the features of claim 1, a closure comprising such a receptacle with the features of claim 15, and a container with the features of claim 16. Preferred embodiments follow from the other claims.

According to one aspect, a subject of the invention is a receptacle intended to regulate the atmosphere in a container for storing sensitive products, wherein the receptacle is designed for forming a chamber which is at least partially filled with an active substance for atmosphere regulation, the receptacle comprising a body and a cap configured to close the body, wherein the cap comprises a top wall with a first main side facing the interior of the chamber, and a skirt integrally formed with the top wall, and the body comprises a bottom wall and a sidewall extending from the bottom wall and being integrally formed with the bottom wall, the skirt of the cap and the sidewall of the body being dimensioned and mutually arranged to surround one another in contact with each other in an overlapping region in the closed configuration of the receptacle, so that the chamber is delimited by the bottom wall of the body, the top wall of the cap and the skirt of the cap and/or the sidewall of the body, wherein at least one ventilation path, comprising at least one recess in at least one of the cap and the body, is provided between the skirt of the cap and the sidewall of the body, such that the ventilation path connects the chamber with the atmosphere in the container outside the receptacle. In other words, the overlapping region comprises a contact region between the cap and the body (abutting relationship) and a "non contact" region provided by the at least one ventilation path.

The at least one ventilation path is provided in an overlapping region between the skirt and the sidewall. The term ventilation path describes any voids between the sidewall and the skirt which enable air communication within the sidewall ventilation path. At least one section of each ventilation path connecting the chamber with the atmosphere in the container has very small dimensions so that dust escaping from the chamber gets stuck and cannot escape to the outside atmosphere. In view of the dust being a particulate matter, one dimension of the ventilation path should be selected small enough so that the dust cannot pass through the ventilation path. The provision of the at least one ventilation path between the cap and the body is advantageous because its size can be controlled with a high accuracy because of the abutting relationship between the cap and the body of the receptacle, the at least one ventilation path being adjacent to a contact between the cap and the body.

According to one embodiment, at least one section of the at least one ventilation path connecting the chamber with the atmosphere in the container has a cross-sectional dimension of 0.2 mm or less, preferably 0.1 mm or less, more preferably 0.05 mm or less. Within the meaning of the invention, a cross-sectional dimension of the ventilation path is a dimension taken transversely to the direction of circulation of gases or particles in the ventilation path between the chamber and the atmosphere in the container. In one embodiment of the receptacle according to the invention, the active substance is received in a chamber delimited directly by walls of the cap and the body, without any porous membrane for retaining the active substance in the inner volume of the chamber. Then, the ventilation path is configured to allow passage of gases between the chamber and the atmosphere in the container, while preventing escape of the active substance from the chamber toward the atmosphere in the container.

Such small structures required for the at least one ventilation path like small depressions or ribs forming voids between two consecutive ribs can be formed with injection molding machines using molds which are precision machined by micromachining or nanomachining.

The chamber of the receptacle is formed by two separate elements which can be fit one onto the other. In order to ensure that there is a sufficient exchange of air, the at least one ventilation path is provided which transports air between the chamber filled with an active substance and the atmosphere outside the receptacle.

As soon as the receptacle is arranged inside a closed container, the atmosphere outside the receptacle has to be understood to be the atmosphere within the closed container.

The inventive solution has the advantage that the active substance within the chamber of the receptacle is firmly contained therein and will not inadvertently leak out.

Further, the solution according to the invention can form the receptacle exclusively from pharmaceutically suitable plastic material. Finally, the solution according to the invention speeds up the assembly of the receptacle because the process of connecting the cap and body consumes less time as compared to the closing of the chamber by means of a crimping or welding process.

A further advantage of the inventive receptacle is that it is possible only to fill the chamber partially with an active substance without the risk of loosening the cardboard disc as used in the prior art. Further, the assembly is faster than the technology of hot crimping a permeable disc.

A further advantage of the inventive solution is that both the cap and the body can be made of the same material.

Alternatively, either the cap or the body can be made of a plastic material which is more permeable than the plastic material of the other element. The material of the cap and/or the body can be selected depending on its permeability for the gas that needs to be trapped by the active substance. For example, one of the cap or the body can be made from a material of high moisture permeability whereas the other of the cap or the body can be made from a material with high oxygen permeability. Advantageously, any of the cap and the body can be made of a material comprising the active substance blended with a plastic material, for example a desiccant entrained polymer.

The at least one ventilation path can be dimensioned such that it forms at least a part of an unobstructed path which is formed between the chamber and the atmosphere outside the receptacle. In case of e.g. desiccant particles, the dimensions of the at least one ventilation path can be selected such that the desired exchange of the air will not be impeded by a single particle within the chamber which might obstruct the free cross-section of the ventilation path. In the same way, the cross-sectional shape of the ventilation path should be selected such that a particle of the active substance cannot enter and get stuck therein. If the particles of the active substance create some dust particles which are small enough to get stuck in the ventilation path, they cannot obstruct completely the ventilation path.

A ventilation path can be formed by any recessed geometry bounded by elevated structures. It can be a conventional groove extending into the sidewall of the body. It can also be formed between ribs extending out of the sidewall. Further, the ventilation paths might also cross each other. The ventilation path can also be formed by a suitable geometry formed in both the skirt and the sidewall.

The inventive receptacle covers two different solutions. Either the skirt is arranged outwards of the sidewall, or the sidewall is arranged outwards of the skirt.

The inventive receptacle can be used for any active substance.

Active substances are capable of absorbing various different pollutants such as humidity, oxygen, odour and other possible pollutants, and thus capable of regulating the atmosphere in a container. They belong to a group of humidity absorbers, oxygen scavengers, odour absorbers and/or emitters of humidity or volatile olfactory organic compounds. Optionally, the active substance can also be capable of releasing gaseous substances such as moisture or perfume. Such property can for example be useful for applications where sensitive products to be stored require a certain humidity level. Such products are, for example, powders, especially for generating aerosols, gelatin capsules, herbal medicine, gels and creams including cosmetics, and food products.

Suitable dehydrating agents are selected from a group comprising silica gels, dehydrating clays, activated alumina, calcium oxide, barium oxide, natural or synthetic zeolites, molecular or similar sieves, or deliquescent salts such as magnesium sulfide, calcium chloride, aluminum chloride, lithium chloride, calcium bromide, zinc chloride or the like. Preferably, the dehydrating agent is a molecular sieve and/or a silica gel.

A suitable oxygen collecting agent is selected from a group comprising metal powders having a reducing capacity, in particular iron, zinc, tin powders, metal oxides still having the ability to oxidize, in particular ferrous oxide, as well as compounds of iron such as carbides, carbonyls, hydroxides, used alone or in the presence of an activator such as hydroxides, carbonates, sulfites, thiosulfates, phosphates, organic acid salts, or hydrogen salts of alkaline metals or alkaline earth metals, activated carbon, activated alumina or activated clays. Other agents for collecting oxygen can also be chosen from specific reactive polymers such as those described for example in the U.S. Pat. No. 5,736,616, WO 99/48963, WO 98/051758 and WO 2018/149778.

In another embodiment, the active material is a material able to establish a 2-way humidity control, e.g. trapping moisture from the environment when the environment is too humid, or releasing moisture to the environment when the environment is too dry.

In one embodiment, the receptacle according to the invention is made of a suitable plastic material which is preferably selected from the group comprising radical or linear high and low density polyethylenes, copolymers of ethylene such as for example ethylene vinyl acetates, ethylene ethyl acrylates, ethylene butyl acrylates, ethylene maleic anhydrides, ethylene alpha olefines, regard-less of the methods of polymerisation or modification by grafting, homo polypropylene and copolymers, polybutene-1, polyisobutylene. Polyolefines are preferably selected to make the receptacle for cost reasons and because they are easy to use.

Other polymer materials can be considered however such as polyvinyl chloride, copolymers of vinyl chloride, polyvinylidene chlorides, polystyrenes, copolymers of styrene, derivatives of cellulose, polyamides, polycarbonates, polyoxymethylenes, polyethylene terephthalates, polybutylene terephthalates, copolyesters, polyphenylene oxides, polymethyl methacrylates, copolymers of acrylate, fluoride polymers, polyphenylene sulphides, polyarylsulphones, polyaryletherketones, polyetherimides, polyimides, polyurethanes, phenol resins, melamine resins, urea resins, epoxy resins and unsaturated polyester resins.

Biodegradable polymer materials, with for example a starch base, are also possible such as polylactic acids (PLA).

Combinations of these polymers can be used, if desired. The polymer used to produce the receptacle can also contain one or more additives such as fibers, expanding agents, additives such as stabilizers and colorants, sliding agents, demolding agents, adhesion agents or reinforced catching agents and/or any others according to the requirements of usage.

According to one embodiment, the sidewall and the skirt have a substantially tubular shape.

The tubular shape covers any cross-section with a closed wall of the sidewall and of the skirt. Tubular shapes can be e.g. circular, oval or square-shaped.

However, it is especially advantageous to provide a circular cross-section for the sidewall and the skirt. Such a shape has the advantage that the attachment of the body to the cap is simplified, because no specific rotational orientation of the body relative to the cap is required.

According to one embodiment of the invention, the at least one ventilation path comprises a groove with a depth of 0.2 mm or less, preferably 0.1 mm or less, and more preferably 0.05 mm or less. Small dimensions of 0.1 mm or even 0.05 mm either in the depth direction or in the width direction are preferred so that the receptacle can also be used for storing liquids and powders with a small particle size. When nano machining or micro machining is used, the ventilation path can have dimensions with a cross-section, the smallest dimension of which is smaller than 0.05 mm.

The provision of a cap leaves a receptacle body with dimensions which are sufficient to fill in an active material before, in the course of the production process, the cap is closed on the receptacle body.

According to one embodiment, the at least one ventilation path connecting the chamber with the atmosphere in the container comprises at least two recesses distributed in a circumferential direction of the receptacle in the closed configuration thereof, so that the formed ventilation path is a tortuous ventilation path.

According to one embodiment, the skirt surrounds the sidewall, and the skirt is provided with a plurality of indentations in an inner circumferential surface of the skirt. The plurality of indentations serve to form part of a ventilation path, respectively so that in the overlapping part of the skirt and the sidewall, the indentations form voids which are at least a part of each individual ventilation path.

According to one embodiment, when the skirt surrounds the sidewall, the sidewall has a plurality of depressions in an outer circumferential surface of the sidewall. Such depressions of the sidewall, together with a plurality of indentations in the inner circumferential surface of the skirt, are forming segments of a suitable ventilation path.

According to one embodiment, at least one depression in the outer circumferential surface of the sidewall has an extension in a circumferential direction of the sidewall which exceeds the extensions of other depressions in a circumferential direction of the sidewall.

A circumferential gap is provided in the overlapping region between the skirt and the sidewall. It serves to simplify the production of the receptacle because in case of a circular cross-section of the skirt and of the sidewall, no specific mutual orientation of the skirt relative to the sidewall needs to be considered and at least one ventilation path will be automatically provided. Air can travel from the outside to the inside of the receptacle, following a path formed by the depression(s) the circumferential gap between skirt and sidewall, the indentations, the crenels a top of the sidewall. Such a complex path, with multiple changes in direction, combined with the reduced depth or width of the depression and or indentation makes it nearly impossible for a dust particle to travel from the inside of the receptacle to the outside. Surprisingly, it has been found that this makes the receptacle is also suitable for storing liquid in a leak proof manner, especially viscous liquids such as saturated salt solutions.

According to one embodiment of the invention, the number of indentations in an inner circumferential surface of the skirt differs from the number of depressions in an outer circumferential surface of the sidewall. In such a case, it is even possible to select an equidistant arrangement of the indentations and of the depressions because by an appropriate selection of the number of indentations and number of depressions as well as their individual sizes, it can also be ensured that irrespective of the relative angular orientation of the cap relative to the body, chances that at least one indentation will come to lie at one depression will be minimized such that the ventilation path becomes more tortuous. In particular, air entering the receptacle and more importantly contents liable to escape from the receptacle will have to travel in different directions.

According to one embodiment of the invention, the end of the sidewall is a crenelated rim or the end of the sidewall is a micro textured surface. A crenelated rim has the advantage that the passage of ventilation air is even possible in case that the sidewall of the body extends up to the top wall of the cap. In such a case, the crenels allow the passage of air so that air which travels between the sidewall and the skirt can pass through the crenels into the chamber.

According to one embodiment, the difference of height between merlons and crenels of the crenelated rim is 0.2 mm or less, preferably 0.1 mm or less, more preferably 0.05 mm or less. Such a small dimension prevents an active substance from passing through the small slits formed by the crenels. This makes it even possible to use the receptacle for storing liquids in a leak-tight manner. For example, instead of containing a desiccant in granulated or powder form, the receptacle can contain a liquid, for example a saturated salt solution. Some saturated salt solutions are known to maintain the relative humidity at a specific value. The chamber of the receptacle filled with such a liquid can be used to keep pharmaceutical healthcare and other products at a constant and regulated moisture level when they are stored in a package or container comprising such a receptacle.

According to one embodiment, the cap is fixed to the body by friction in an abutting region between the skirt and the sidewall.

The provision of a friction fit is the easiest way to attach the cap to the body.

As an alternative or additional measure, a further embodiment of the invention designs the cap and body of the receptacle such that they are connected by means of a snap-fit connection.

A snap-fit connection has the advantage that in case of small manufacturing tolerances, this will only have little influence on the connection force of a snap-fit connection whereas in case of a friction fit between the cap and the body, small manufacturing tolerances can have a high influence on the resulting holding force.

In one embodiment, the receptacle is made of a plastic material. The use of a plastic material makes it possible to use manufacturing technologies which are suitable for an automated production of high numbers of receptacles. Further, it is possible to manufacture the receptacle from a plastic material which is pharmaceutically approved.

According to one embodiment of the invention, the cap and/or the body comprise a wall which has a predetermined permeability to gas.

The provision of a wall with a predetermined, defined permeability to gas constitutes an additional transport mechanism in addition to the transport of air through the at least one ventilation path. It can have the further advantage that the active substance within the chamber becomes more uniformly loaded if the wall which is permeable to air is remote from the position at which the at least one ventilation path communicates with the interior of the chamber.

Another subject of the invention is a closure for closing an open end of a container body part, said closure comprising a receptacle as described above, wherein the closure is provided with a base with a first main side facing the interior of the container when closing the container, wherein the receptacle is preferably attached to the first main side of the base of the closure, most preferably by means of a snap-fit connection. However, the receptacle can be fixed to the closure in any suitable way, for example by adhesion or using a fixing and/or fastening element.

Finally, the invention also relates to a container for storing loose products comprising a container body part with an openable or removable closure, and a receptacle as described above. Such a container can be used for storing moisture or oxygen sensitive products, especially pharmaceutical products, in particular drugs, pills, tablets, globuli, granulates, lozenges, test strips or powder. The body part of the container can be of any shape including a cylindrical shape with a round, oval or polygonal base.

However, apart from cylindrical shapes, the container body part can be of any geometry including irregular shapes.

BRIEF DESCRIPTION OF THE DRAWINGS

In the following, the invention will be described by way of example with reference to the accompanying drawings, in which.

DESCRIPTION OF EMBODIMENTS

In the following, two major embodiments of the invention will be described. Wherever appropriate, the same elements will be denoted by the same reference numerals.

As will be shown below with reference to the specific embodiments and its variants, the major difference between the first major embodiment according to FIGS. 1 to 6 and the second major embodiment according to FIGS. 7A to 12 lies in the mutual arrangement of the skirt of the cap 10 and the sidewall of the body 20.

Figure 1:
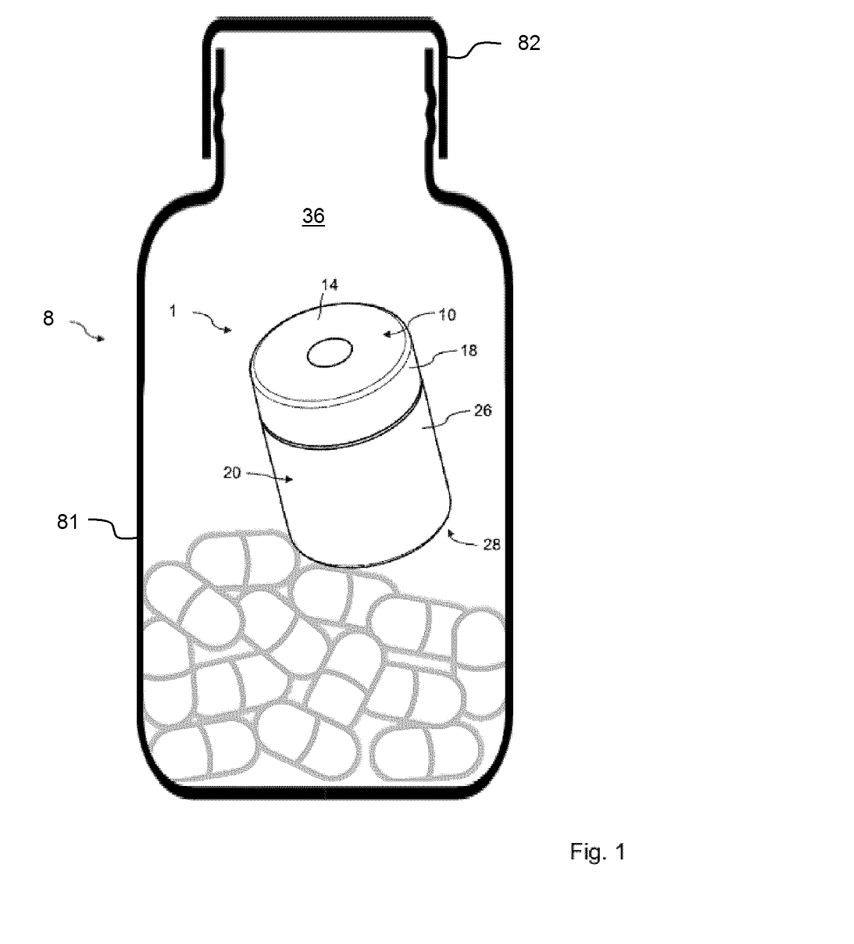
FIG. 1 shows a first embodiment of a receptacle according to the invention, dropped in a container filled with sensitive pharmaceutical products.

The receptacle as shown in FIG. 1 is a canister 1, comprising a cap 10 and a body 20. The cap 10 comprises a top wall 14 and a skirt 18. The top wall 14 is integrally provided with the tubular skirt 18.

The body 20 comprises a bottom wall 28 and a tubular sidewall 26 which is integrally provided with the bottom wall 28.

As shown in the example of FIG. 1, the canister 1 is dropped in a container 8 for storing sensitive products, e.g. pharmaceutical products.

The sidewall 26 of the canister body 20, which is integrally formed with the bottom wall 28, has a substantially tubular shape and extends perpendicularly from the bottom wall 28. In the first embodiment as shown in FIGS. 1 to 6, the outer diameter of an upper portion 21 of the sidewall 26 is selected such that it can be placed, at least partially, inside the skirt 18.

The sidewall 26 of the canister body 20 is dimensioned so that the skirt 18 of the cap 10 is held by a snap-fit connection (protruding part 210 on the upper portion 21 of the sidewall 26 in interaction with the protruding part 110 on the inner side of the skirt 18 of the cap 10).

In the embodiment according to FIG. 1, a snap-fit connection is used. This can be best seen in the cross-sectional view in FIG. 2 which shows the canister body 20 with the bottom 28 and sidewall 26, and the cap 10 with its top wall 14 and the skirt 18. In order to stiffen the overall structure, FIG. 2 additionally shows a reinforcing rib 90 on that side 16 of the top wall 14 of the cap which faces the interior of the canister 1, and a reinforcing rib 92 on the inner side of the bottom 28 of the canister body 20.

Figure 2:
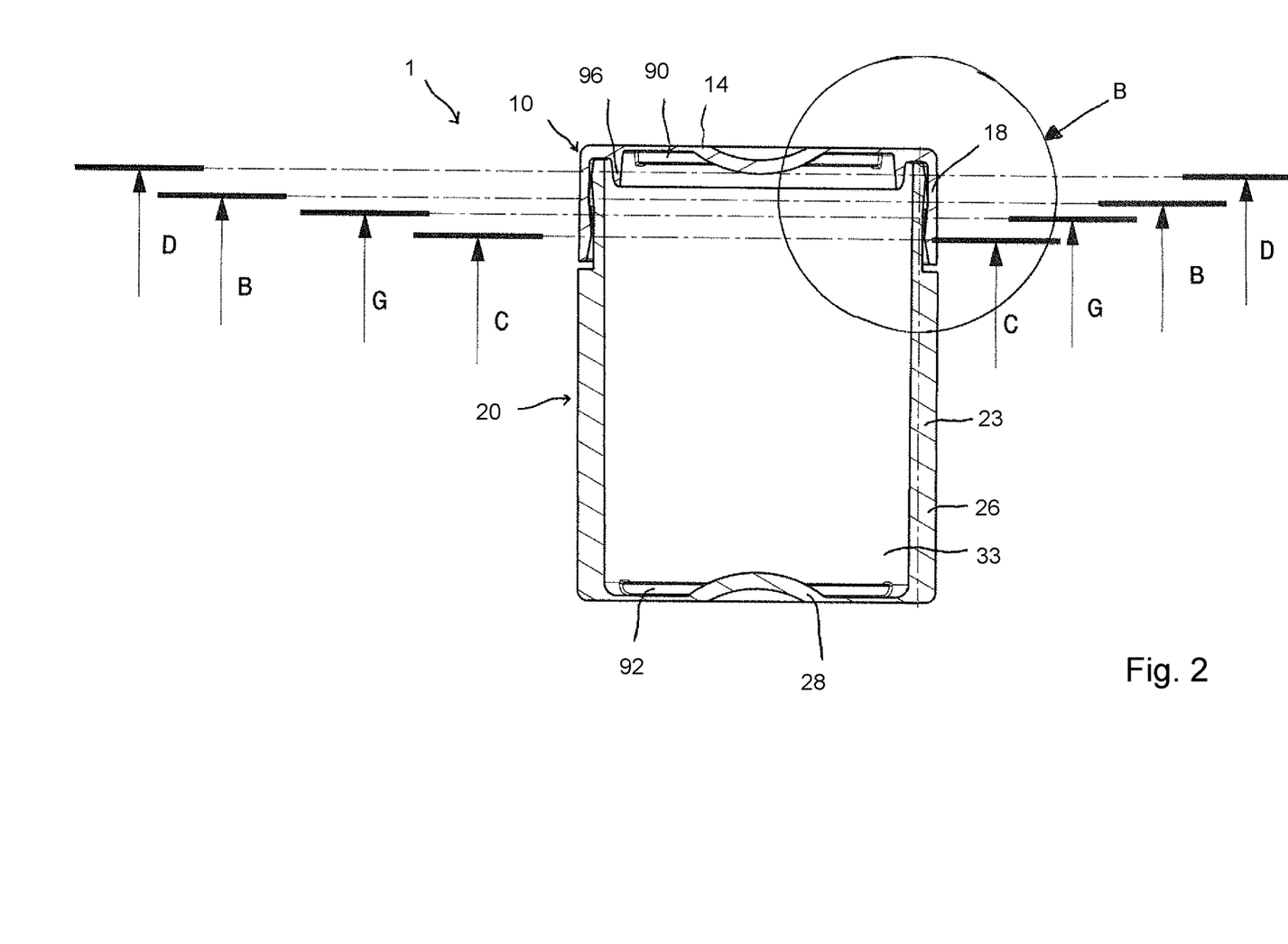
FIG. 2 shows a cross-sectional side view of the receptacle according to the embodiment of FIG. 1.
Figure 2A:
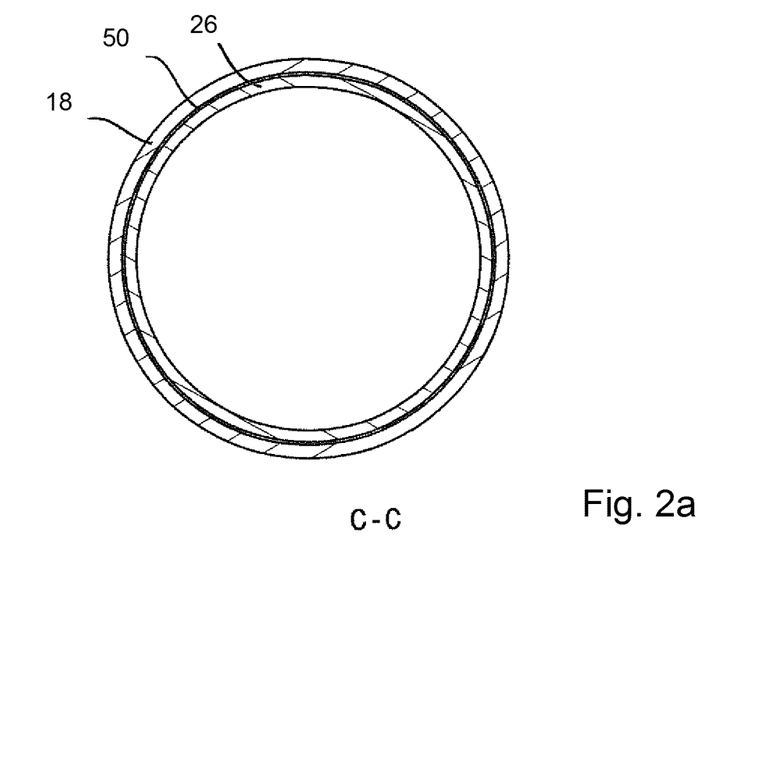
FIG. 2a shows a cross-sectional side view along lines C-C in FIG. 2.
Figure 2B:
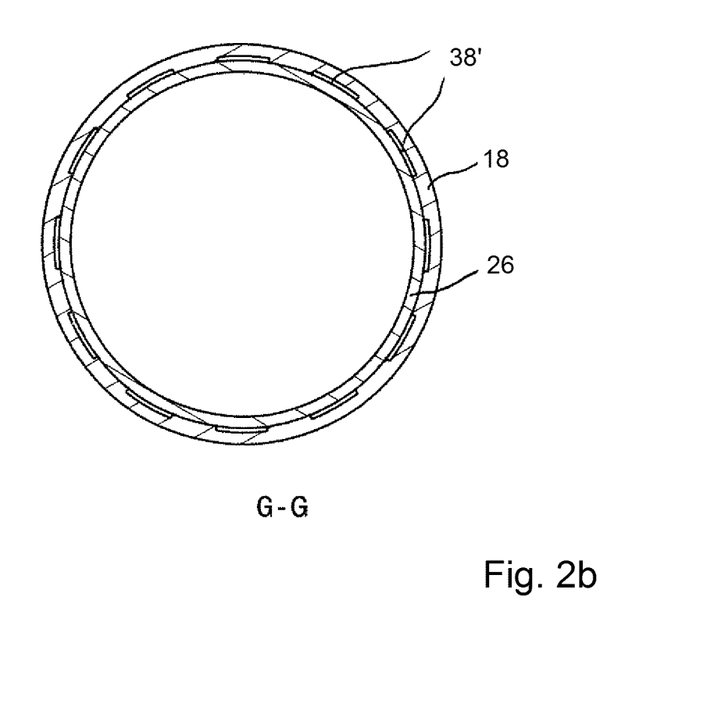
FIG. 2b shows a cross-sectional side view along lines G-G in FIG. 2.
Figure 2C:
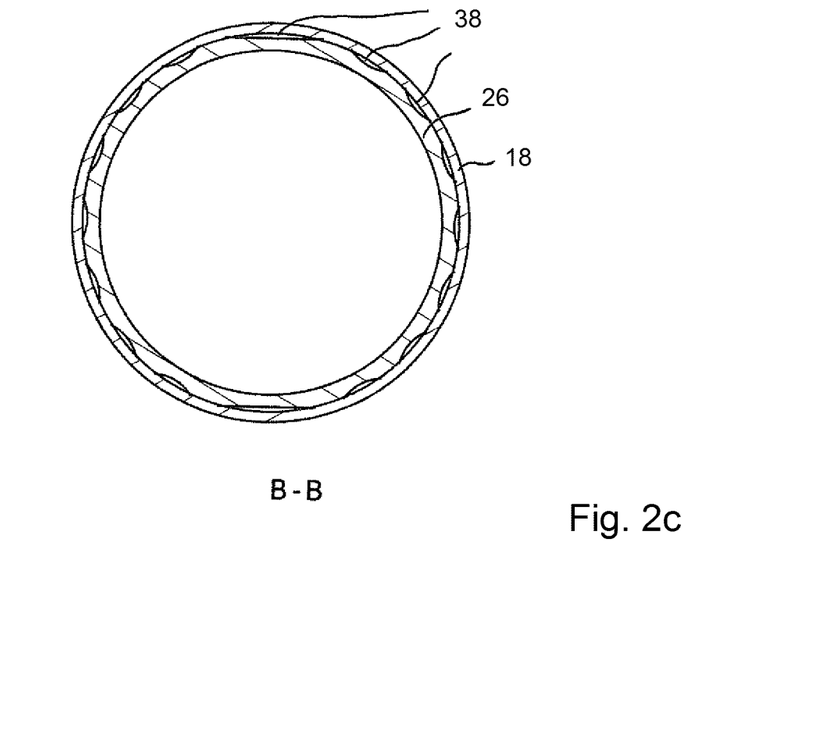
FIG. 2c shows a cross-sectional side view along lines B-B in FIG. 2.
Figure 2D:
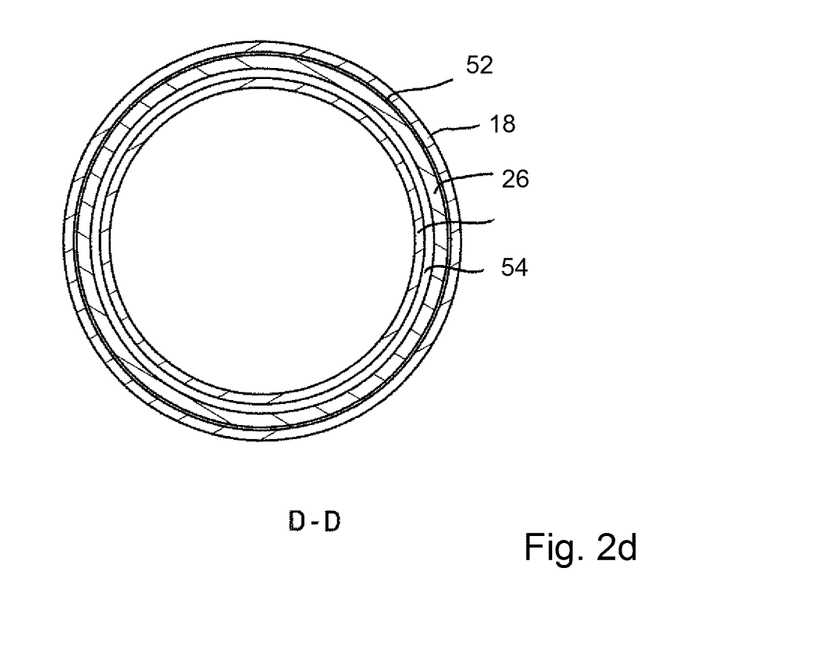
FIG. 2d shows a cross-sectional side view along lines D-D in FIG. 2.

As can be seen in FIG. 2, the mutual arrangement of the skirt 18 and the sidewall 26 is such that the skirt 18 is positioned radially outwards relative to the upper portion 21 of the sidewall 26. The upper end of the sidewall 26 as well as the inner circumferential surface of the skirt 18 are shaped and adapted to establish a snap-on fit between the cap 10 and the body 20 when the skirt 18 of the cap 10 laterally surrounds the body 20.

Figure 3:
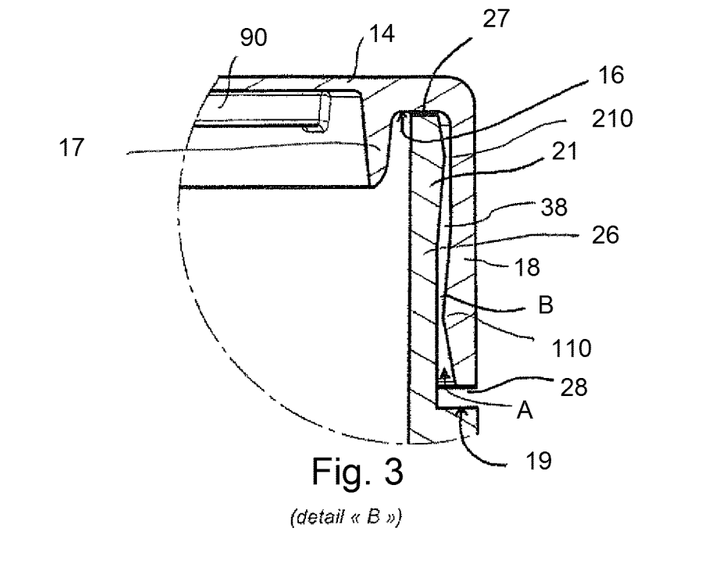
FIG. 3 shows the detail "B" as shown in FIG. 2.

The sidewall 26 of the body 20 can comprise a step 19 as shown in FIG. 3 which is formed between an upper portion 21 of the sidewall 26 located adjacent to the upper opening and a second portion 23 of the sidewall 26 located beneath the first, upper portion 21, wherein the first portion 21 is at least partially thinner than the wall thickness of the lower portion 23 so as to form the step 19. The snap-fit connection can be designed as described in WO 2015/139954.

Alternatively, the lower portion 23 can be as thin as the upper portion 21 and can optionally be reinforced by vertical ribs (either in the inner side or on the outer side of the sidewall 26).

In the detailed view of FIG. 3, it can be seen that there is a ventilation path B formed by an indentation 38' on the skirt of the cap 10 which allows air to enter in the direction of arrow A in a free space between the skirt 18 and the sidewall 26 of the canister body 20. The ventilation path further comprises a depression 38 on the canister body 20 which can be best seen in FIG. 4 and the detail view thereof in FIG. 5 and a crenelated structure at the upper rim 27 of the sidewall 26.

Figure 5:
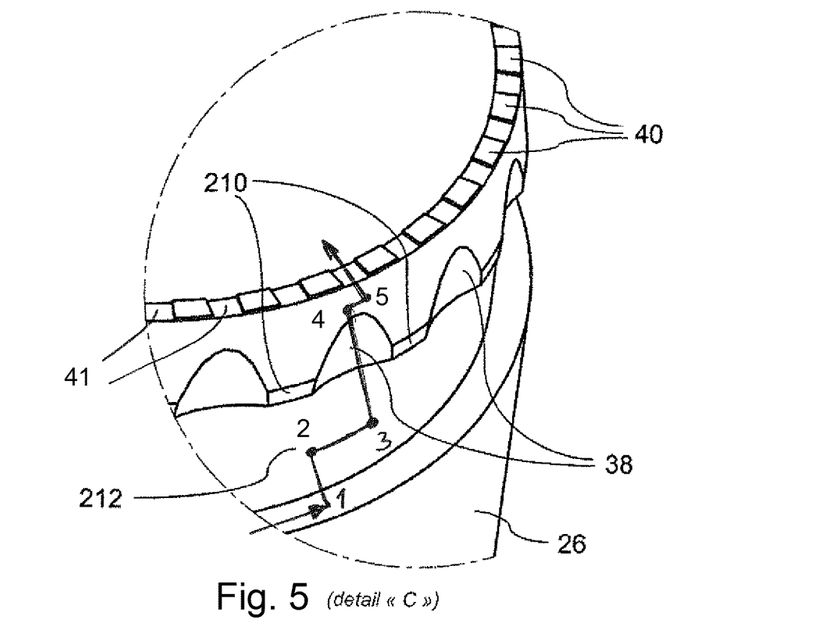
FIG. 5 shows the detail "C" as marked in FIG. 4.
Figure 6:
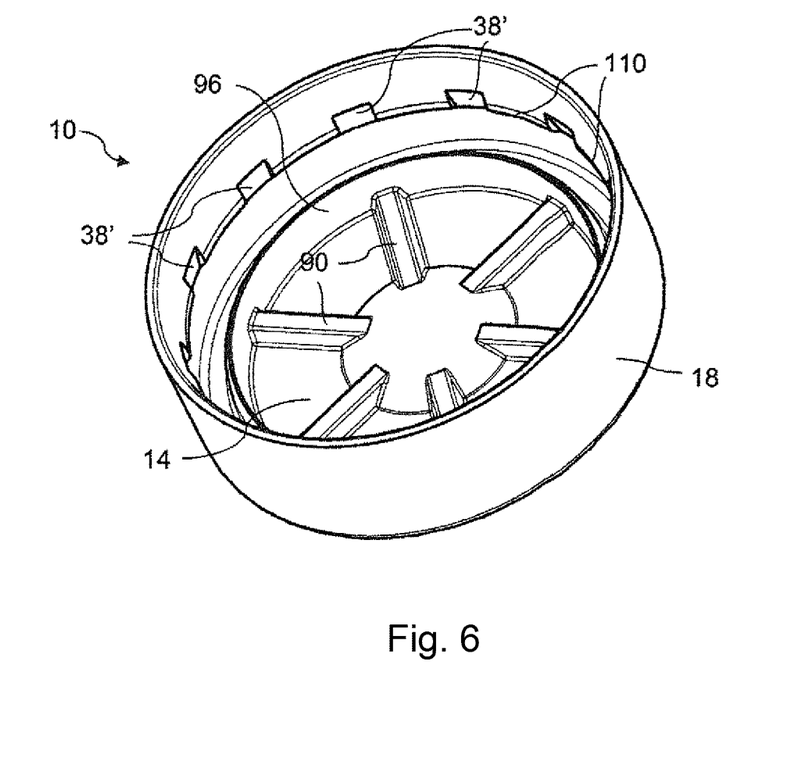
FIG. 6 shows the cap of the receptacle according to the embodiment of FIGS. 1 to 5 above.

Further, in FIG. 5, a recessed part 212 on the sidewall 26 of the canister body 20 is shown. This recessed part forms the undercut which is used for the snap-fit connection of the correspondingly shaped skirt 18 of the cap 10 with a radially inwards directed protrusion which can be accommodated in the recessed part 212 after the snap-fit connection has been achieved.

Between protruding parts 210 on the sidewall 26, there are a plurality of depressions 38 around the outer circumference of the sidewall 26 which, when the skirt 18 of the cap 10 is fitted onto the sidewall 26, form individual ventilation spaces which are a part of a ventilation path and which allow for a gas exchange between the atmosphere 36 out of the canister 1 and the interior chamber 33 therein. In other words, a peripheral protruding part 210 on the sidewall 26 is interrupted by a plurality of depressions 38 such as to form a plurality of ventilation spaces which are a part of a ventilation path.

As can be seen in FIG. 3, the distal end of the sidewall 26 partially abuts against the side of the top wall 14 of the cap 10 which faces the interior of the canister 1. In order to allow an unobstructed exchange of air in that part, the upper rim 27 of the sidewall 26 is provided with a crenelated structure with merlons 40 and crenels 41 in-between. The at least one ventilation path thus comprises at least one crenel 41. Since the height difference between the merlons 40 and crenels 41 is very low, even an active substance within the canister 1 which is either a powder or even a liquid, like a salt solution, cannot escape the chamber 33 inside the canister. For any particulate matter, it cannot pass through the small slits formed by the crenels 41, whereas in case of a liquid, the strong capillary effect will keep such liquid within the small slits formed by the crenels so that liquid can also not escape through the ventilation path. The crenels 41 can be regularly or irregularly distributed on the upper rim 27. Micro texturing of the upper rim 27 top surface has been found to be well suitable to create a gaseous path but still allows the canister 1 to stay liquid tight. Such a micro structure can be obtained from micro- or nano machining of the mold cavity and can be associated with Heat and Cool Injection Molding Technology which has proven to be efficient in improving the surface definition of the molded upper rim 27.

The unobstructed ventilation path further comprises ventilation spaces 38' on the interior circumferential surface of the skirt 18 of the canister cap 10 which, irrespective of the mutual orientation of the depressions 38 on the canister body 20 and the ventilation spaces 38' together form part of one ventilation path. Preferably, the width or circumferential extension of a ventilation space 38' is greater than the circumferential extension of a depression 38.

When the canister cap 10 is fixed on the canister body 20, the depressions 38 will be provided in a position between the ventilation spaces 38' on the canister body 20 and the upper rim 27 of the sidewall on which the merlons 40 and crenels 41 are provided. The provision of the crenels 41 and the mutual arrangement of the ventilation spaces 38' and the depressions 38 lead to a winding ventilation path. Such a tortuous path provides an additional obstacle for the inadvertent passage of small particles, like broken fragments of an active substance which might enter the ventilation path.

In FIG. 5, a schematic ventilation path is shown as a possible example. First, air enters in the direction of arrow A the gap formed between the step portion 19 and the lower end (distal end) of the skirt 18 of the cap 10 (see FIG. 3). The air arrives at point "1" in FIG. 5. After that, the air travels through an indentation 38' to point "2" in FIG. 5 (see also FIG. 2*b*). The ventilation path continues in a circumferential direction in a first gap 50 formed between the sidewall 26 of the canister body 20 and the skirt 18 of the cap 10 to point "3" in FIG. 5 (see FIG. 2*a*). Then, the ventilation path continues in a vertical direction through a depression 38 to point "4" in FIG. 5 (see also FIG. 2*c*). The ventilation path continues in a circumferential direction in a second gap 52 formed between the sidewall 26 of the canister body 20 and the skirt 18 of the cap 10 to point "5" in FIG. 5 (see also FIG. 2*d*). Then, the air travels through a crenel followed by a vertical movement through a third gap 54 formed between the inner surface of the sidewall 26 of the canister body 20 and the inner skirt 96 of the cap 10, and into the interior of the canister 1 (see also FIG. 2*d*). Both the first gap and the second gap do not necessarily have to run all around the respective circumference as long as at least one continuous ventilation path is established.

Preferably, the indentations 38' and depressions 38 are angularly offset relative to each other so that a particle escaping from the inside of the canister 1 needs to travel a tortuous path running in multiple directions.

Figure 4:
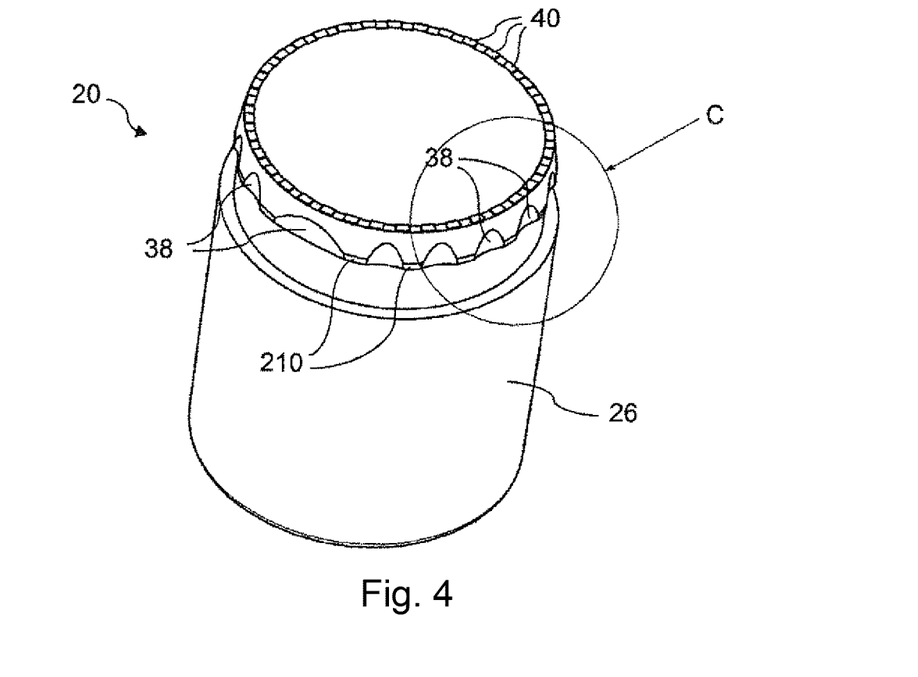
FIG. 4 shows the receptacle according to FIG. 1 without the cap.

As can be seen in FIG. 4, the circumferential extensions of the individual depressions 38 are not the same. There is at least one depression 38, preferably at least two depressions 38, the circumferential extension of which exceeds that of the other depressions 38. The reason is that, for molding process by slide parts of the mold due to the undercut 212 of the canister body 20, the slides are joined on the larger depressions 38.

As an alternative, the number of depressions 38 could differ from the number of ventilation spaces 38', or either the depressions or ventilation spaces could be distributed around the circumference of the sidewall and skirt so that they are not equidistantly spaced. Any such measures either alone or in combination serve to generate at least one ventilation path no matter in which orientation the cap 10 is attached to the canister body 20. Further to the better ventilation, different numbers of depression 38 and 38' allows to guarantee a strong snap-fit between the protrusions 210 and the protrusions 110 whatever the orientation of the cap 10 regarding the canister body 20 (better holding with larger hook 110).

Another embodiment of the invention is described in FIGS. 7A to 12. One major difference is the cross-sectional shape of the canister 1 which, in the second embodiment, is of a roughly square shape with flattened or rounded corners. A further major difference lies in the fact that, in the embodiment according to FIGS. 7A to 12, the skirt of the cap is surrounded by the sidewall of the canister 1. These and further differences will be detailed below.

Figure 7A:
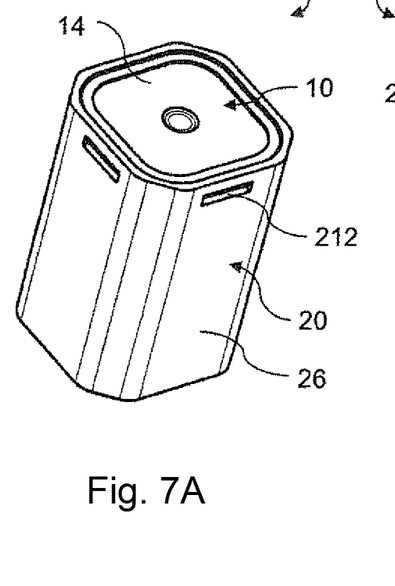
FIG. 7A and FIG. 7B show a second embodiment of a receptacle according to the invention.
Figure 7B:
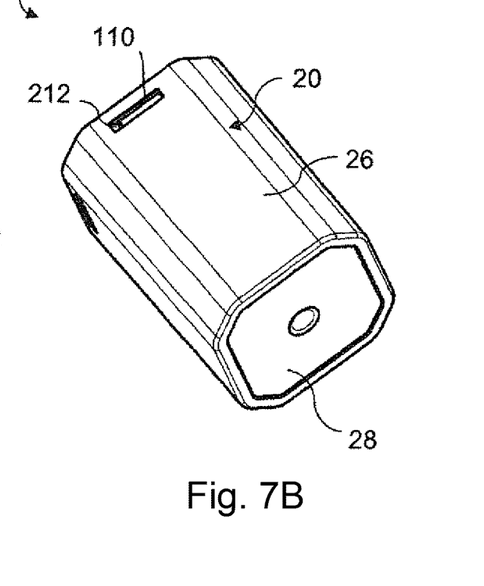

In the two views of FIGS. 7A and 7B, the receptacle is a canister 1 which also consists of two elements. The cap 10 closes the canister body 20. The canister body 20 comprises a bottom wall 28 and a sidewall 26 which extends perpendicularly from the bottom wall 28 and is provided as a unitary structure with the bottom wall 28. The cap 10 closes an open end of the sidewall 26 of the canister body 20.

Figures 8A, 8B:
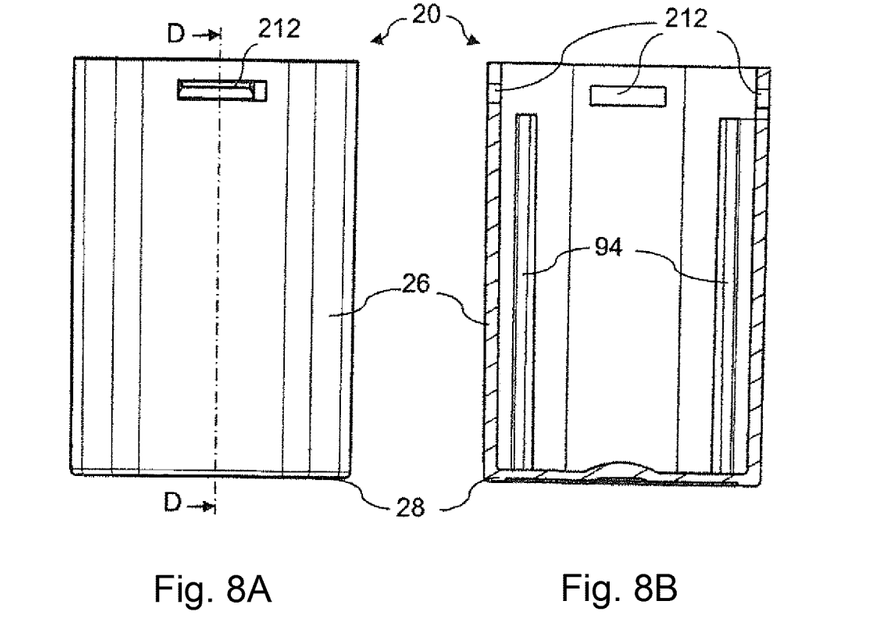
FIG. 8A shows a side view of the receptacle according to FIG. 7A.
FIG. 8B shows a cross-sectional view along the lines D-D as shown in FIG. 8A.
Figure 9A:
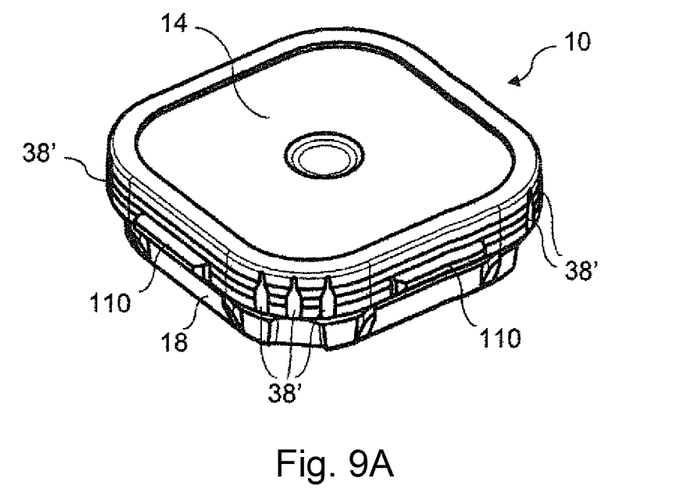
FIG. 9A shows the cap of the receptacle according to FIG. 7A.
Figure 9B:
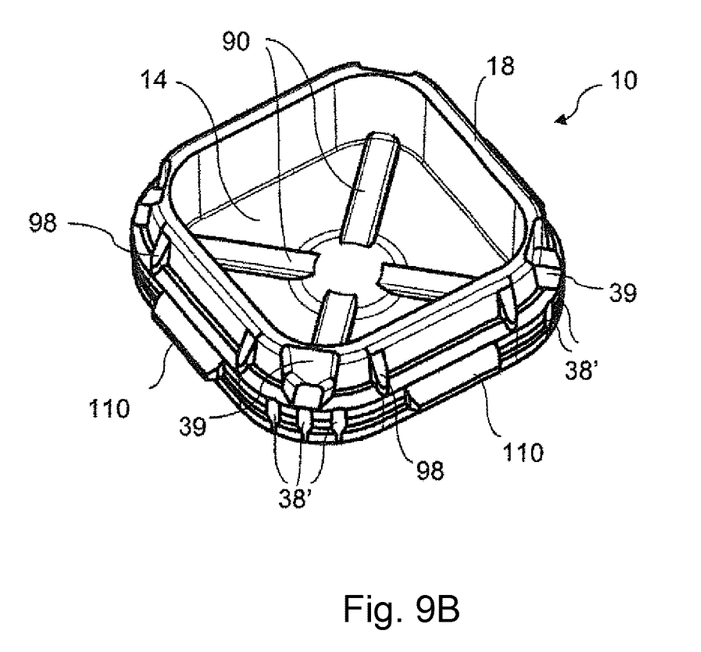
FIG. 9B shows an inside view of the cap as shown in FIG. 9A.
Figure 10:
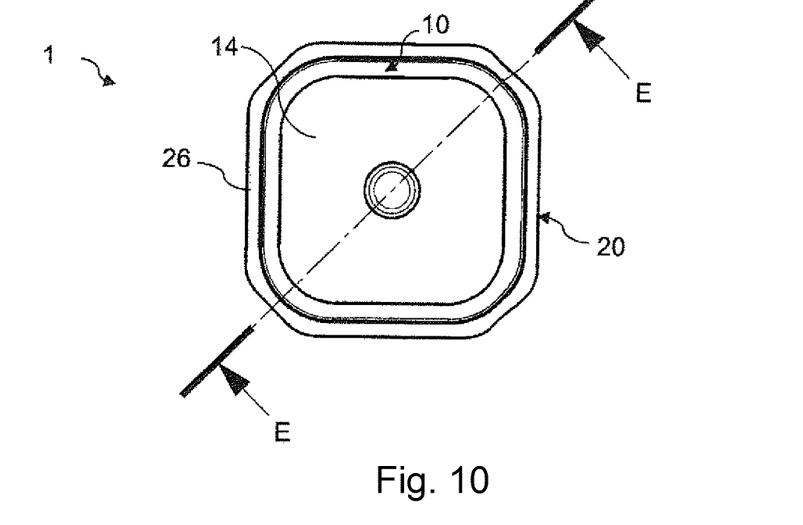
FIG. 10 shows a view from above of the receptacle with the cutting line for a vertical cut through the receptacle according to FIG. 7A.
Figure 11:
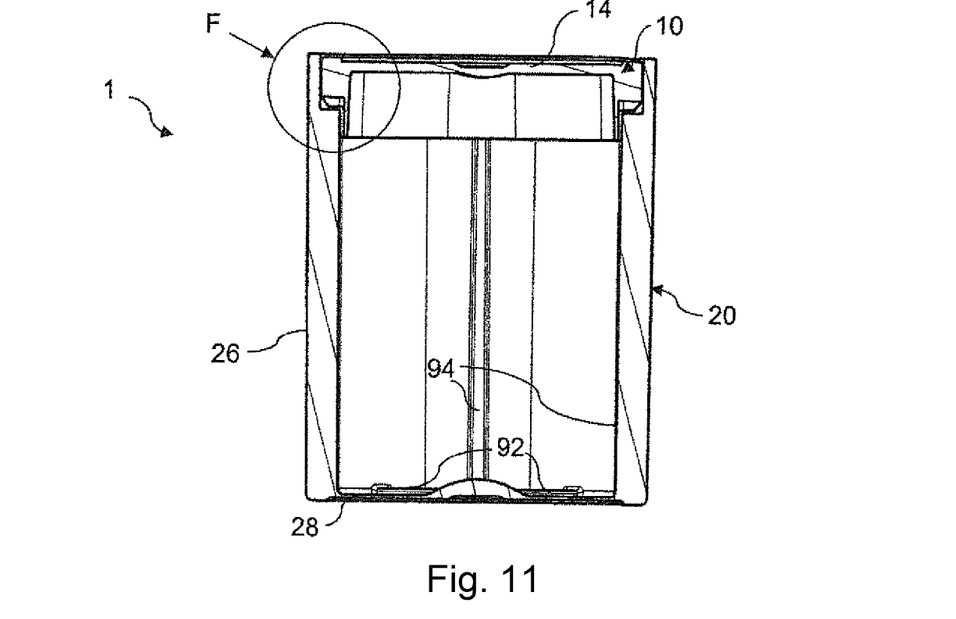
FIG. 11 shows a cross-sectional view along the cutting lines E-E in FIG. 10.
Figure 12:
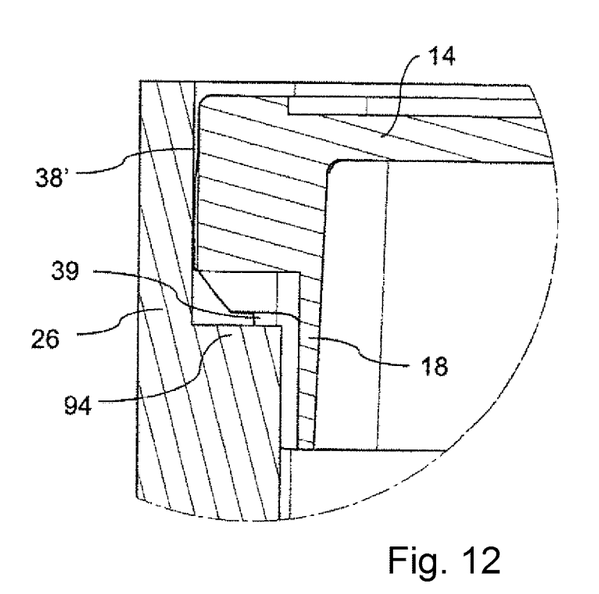
FIG. 12 shows the detail F as indicated in FIG. 11.

In the embodiment according to FIGS. 7A to 12, the cap 10 as shown in FIGS. 9A and 9B has a top wall 14 and a skirt 18 which is integrally formed with the top wall 14 and depends therefrom.

All four sides of the skirt 18 are provided with a snapping protrusion 110. When closing the cap 10, the snapping protrusions 110 will snap into and lock inside the recessed parts 212 formed by cut-offs on the sidewall 26 of the canister body 20. In such a way, the cap 10 once closed will firmly be held in place. In order to assist in the establishment of the snap-on fit between the cap 10 and the canister body 20, the snapping protrusions 110 are angled on the lower surfaces so that they can more easily snap into the recessed parts 212 on the sidewall of the canister body 20, whereas it is difficult to remove a cap 10 once assembled from the canister body 20 again.

As can be seen in FIG. 7A, the cap 10 is fixed to the canister body 20 in such a way that the outer surface of the top wall 14 does not extend beyond the upper rim of the sidewall 26 of the canister body 20.

As can be seen in FIG. 8B, the sidewall 26 of the canister body 20 is provided with a plurality of reinforcing ribs 94 which stiffen the sidewall of the canister 1. Furthermore, it provides a stop for vertical positioning the cap 10 inside the canister body 20. Likewise, the top wall 14 of the cap 10 is also provided with reinforcing ribs 90 which are provided on that side of the top wall 14 which, in the assembled state, faces the interior of the canister 1. Such ribs allow to use a thinner thickness on the top wall 14 of the cap 10 in order that the top wall is more permeable to gazes.

Further, the skirt 18 of the cap 10 is provided with centering ribs 98, two of which are provided on each side of the skirt. The centering ribs serve for centering the cap 10 relative to the canister body 20 during assembly.

Further, at each rounded or flattened corner of the skirt 18, a recess 39 is formed which is part of the ventilation path. In addition to the recess 39, several vents 38' are provided in the skirt 18 of the cap 10 which can be best seen in FIGS. 9A and 9B. Furthermore, these recesses 39 provide a location for ribs 94 of the canister body 20. From the cross-sectional view in FIG. 11 and, as an enlarged detail F, in FIG. 12, it can be seen that between the cap 10 and the canister body 20, a small ventilation path for air is formed by the vents 38' as well as the recesses 39 which have the effect that the cap rests on the upper end of the ribs 94 inside the canister body 20 and which extend into the recesses 39 in the skirt 18 of the cap 10. In such a way, a tortuous path is formed which represents the ventilation path connecting the interior of the canister 1 to the outside atmosphere 36.

Throughout the embodiments, it is possible to either add the canister 1, filled with an active material, to the interior of a container 8 as a loose part, as illustrated schematically in FIG. 1, or to affix the canister 1 in a suitable way to a closure 82 closing a container 8 for storing moisture or oxygen sensitive products. Especially, such a container 8 might contain a pharmaceutical product, in particular drugs, pills, tablets, globuli, granulate, lozenges, test strips or powder.

In both embodiments as described above, the canister body 20 and/or the top wall of the cap 10 could be permeable to gas in order to allow fluid exchange between the inside of the canister 1 and the outside atmosphere 36 which, in use, is the inside atmosphere of a container 8 in which the canister is provided. The materials composing the canister body 20 and/or the cap 10 could be selected in regard with the permeation properties of the material for the gas to be absorbed by the canister 1, which makes it possible to mold a canister 1 having a basic fluid exchange for further increasing the exchange kinetic, further to the additional provision of at least one ventilation path.

The invention claimed is:

1. A receptacle to regulate an atmosphere in a container for storing sensitive products, wherein the receptacle forms a chamber which is at least partially filled with an active substance for atmosphere regulation, wherein the receptacle comprises a body and a cap configured to close the body,
    wherein the cap comprises:
        a top wall with a first main side facing an interior of the chamber; and
        a skirt integrally formed with the top wall; and
    wherein the body comprises:
        a bottom wall; and
        a sidewall extending from the bottom wall and integrally formed with the bottom wall;
    wherein the skirt of the cap and the sidewall of the body surround one another in contact with each other in a closed configuration of the receptacle, so that the chamber is delimited by the bottom wall of the body, the top wall of the cap and either the skirt of the cap or the sidewall of the body;
    wherein at least one ventilation path, comprises at least one recess in at least one of the cap and the body and is provided between the skirt of the cap and the sidewall of the body in the closed configuration of the receptacle, such that the ventilation path connects the chamber with the atmosphere in the container; and wherein the at least one ventilation path connecting the chamber with the atmosphere in the container comprises at least two recesses distributed in a circumferential direction of the receptacle in the closed configuration thereof, so that the formed ventilation path comprises a tortuous ventilation path.

2. The receptacle according to claim 1, wherein at least one section of the at least one ventilation path connecting the chamber with the atmosphere in the container has a cross-sectional dimension of 0.2 mm or less.

3. The receptacle according to claim 1, wherein the skirt surrounds the sidewall, and the skirt is provided with a plurality of indentations in an inner circumferential surface of the skirt.

4. The receptacle according to claim 3, wherein the skirt surrounds the sidewall, and the sidewall comprises a plurality of depressions in an outer circumferential surface of the sidewall.

5. The receptacle according to claim 4, wherein the depressions comprise at least one depression with an extension in a circumferential direction of the sidewall which exceeds the extensions of other depressions in a circumferential direction of the sidewall.

6. The receptacle according to claim 4, wherein the depressions in the outer circumferential surface of the sidewall are not equidistantly distributed in a circumferential direction of the sidewall.

7. The receptacle according to claim 4, wherein the number of in indentations an inner circumferential surface of the skirt differs from the number of depressions in the outer circumferential surface of the sidewall.

8. The receptacle according to claim 1, wherein an end of the sidewall is a crenelated rim or the end of the sidewall is a micro textured surface.

9. The receptacle according to claim 8, wherein a difference of height between merlons and crenels is less than 0.2 mm.

10. The receptacle according to claim 1, wherein the cap is fixed to the body by friction between the skirt and the sidewall in at least one abutting region.

11. The receptacle according to claim 1, wherein the cap and the body of the receptacle are connected by a snap-fit connection.

12. The receptacle according to claim 1, wherein the receptacle is made of a plastic material which is pharmaceutically approved.

13. The receptacle according to claim 1, wherein the cap and/or the body comprises a wall which has a predetermined permeability to gas.

14. A closure for closing an open end of a container body part, said closure comprising the receptacle according to claim 1, wherein the closure is provided with a base with a first main side facing an interior of the container when closing the container.

15. A container for storing loose products comprising a container body part with an openable or removable closure, and a receptacle according to claim 1.

16. The receptacle of claim 2, wherein at least one section of the at least one ventilation path has a cross-dimension of 0.1 mm or less.

17. The receptacle of claim 9, wherein the difference of height between merlons and crenels is less than 0.1 mm.

18. The receptacle of claim 9, wherein the difference of height between merlons and crenels is less than 0.05 mm.

19. The closure of claim 14, wherein the receptacle is attached to the first main side of the base of the closure by a snap-fit connection.

* * * * *